United States Patent [19]

Jacobson

[11] Patent Number: 5,434,308
[45] Date of Patent: Jul. 18, 1995

[54] METHOD FOR THE MANUFACTURE OF 3,4'-DIAMINODIPHENYL ETHER

[75] Inventor: Stephen E. Jacobson, Princeton Junction, N.J.

[73] Assignee: E. I. Du Pont de Nemours and Company, Wilmington, Del.

[21] Appl. No.: 183,615

[22] Filed: Jan. 18, 1994

Related U.S. Application Data

[62] Division of Ser. No. 58,961, Apr. 12, 1993, abandoned, which is a division of Ser. No. 685,365, Apr. 15, 1991, Pat. No. 5,202,488.

[51] Int. Cl.$^6$ ............................................. C07C 209/36
[52] U.S. Cl. ..................................... 564/423; 564/273; 564/399; 564/406; 564/430; 564/443
[58] Field of Search ............... 564/419, 430, 423, 406, 564/443, 273, 399

[56] References Cited

U.S. PATENT DOCUMENTS

| | | | |
|---|---|---|---|
| 3,634,519 | 6/1972 | Bentz | 260/612 R |
| 4,329,503 | 5/1982 | Bauer et al. | 564/418 |
| 4,663,484 | 5/1987 | Horstmann | 564/430 |

Primary Examiner—Peter O'Sullivan
Assistant Examiner—Brian M. Burn

[57] ABSTRACT

A method of dehydrogenating 3-amino-2-cyclohexene-1-one with a supported palladium or palladium-platinum catalyst in a solvent in the presence of base to produce 3-aminophenol and its use directly without purification to produce 3,4'-oxydianiline.

4 Claims, No Drawings

METHOD FOR THE MANUFACTURE OF 3,4'-DIAMINODIPHENYL ETHER

This is a division of application Ser. No. 08/058,961, filed on Apr. 12, 1993, now abandoned, which is a divisional application of Ser. No. 07/685,365, filed Apr. 15, 1991 now U.S. Pat. No. 5,202,488, issued Apr. 13, 1993.

FIELD OF THE INVENTION

The present invention relates to a method for manufacturing the polyfunctional intermediate, 3-aminophenol, and, more particularly, a method comprising dehydrogenating 3-amino-2-cyclohexene-1-one (ACO) with a supported palladium or palladium-platinum catalyst in a solvent in the presence of base to produce 3-aminophenol and its use directly without purification to produce 3,4'-oxydianiline, i.e., 3,4'-diaminodiphenyl ether.

DESCRIPTION OF RELATED ART

3-Aminophenol has been prepared by treating resorcinol with ammonia under pressure, or fusion of metanilic acid with sodium hydroxide at elevated temperatures. Resorcinol is obtained commercially by a complicated sulfonation-caustic fusion process. The above processes require either pressure reactors or use highly corrosive chemicals at elevated temperatures and are laborious. Disposal of the excess reactants and solvents requires expensive cleanup of the waste water streams.

U.S. Pat. No. 4,212,823 describes a general procedure for the dehydrogenations of various substituted 3-amino-2-cyclohexene-1-ones to the corresponding 3-aminophenols in the presence of a variety of dehydrogenation catalysts, in an inert solvent at temperatures of 150°-270° C., advantageously in the presence of hydrogen acceptors such as unsaturated materials which can absorb the hydrogen as soon as it is formed to prevent side reactions. In addition, the reactions are run very dilute to minimize intermediate condensation of the 3-amino-2-cyclohexene-1-one with itself or with the 3-aminophenol that is formed. In the case of 3-aminophenol as described in the above patent, a good yield was obtained when one part 3-amino-2-cyclohexene-1-one was dissolved in 50 parts of tetraethylene glycol, one part of 10% Pd on carbon catalyst added and the mass heated to 193°-196° C. At the end of the reaction it was necessary to remove the high boiling solvent by distillation, in order to isolate the product 3-aminophenol.

Canadian Patent 1,026,481 describes a vapor phase process for the preparation of 3-aminophenols from 3-amino-2-cyclohexene-1-ones, but requires special equipment and high temperatures to carry out the desired reaction.

Iida, Yuasa, and Kobayashi in Synthesis, 471 (1982) describe a procedure for preparation of 3-aminophenols in 56% yield by the treatment of 3-amino-2-cyclohexene-1-one with equimolar amounts of mercury (II) acetate in boiling acetonitrile. This procedure may be impractical from a commercial viewpoint because it is necessary to dispose of large amounts of hazardous mercury by-products.

Conversion of 3-aminophenol to 3-aminodiphenyl ethers for use in polymeric syntheses starting with purified 3-aminophenol, is the subject of numerous patents. JP 63-19-503 describes condensing 3-aminophenol with a nitrohalobenzene in the presence of an aprotic polar solvent, such as dimethyl formamide or N-methyl pyrrolidone, in the presence of an alkali metal carbonate while removing the water formed in the reaction as an azeotrope with a hydrocarbon. JP 63017852 (870822) describes a similar process in the presence of quaternary salts. JP 62081358 (870414) carries out the reaction in an aprotic solvent and water while adding an alkali metal hydroxide. JP 60105649 (850611) is similar to the above using an alkali metal carbonate as condensing agent.

EP 0145377 discusses reacting the salt of 3-aminophenol with p-chloronitrobenzene in the presence of a phase transfer catalyst to form the ether. DE 3728139 (89302) describes the reaction of 3-aminophenol salts with nitrochlorobenzene in liquid ammonia under pressure at elevated temperature to form the ether.

SUMMARY OF THE INVENTION

The invention relates to a method for manufacturing 3-aminophenol from 3-amino-2-cyclohexene-1-one by dehydrogenation in the presence of a supported palladium catalyst in a solvent and introducing an amount of base which significantly increases the yield of 3-aminophenol, while requiring much less solvent and catalyst to effect the reaction, thus making the process very attractive from a commercial viewpoint. When the solvent is a tertiary amide the reaction mass, after removal of the catalyst, may be used directly for the synthesis of 3-aminodiphenyl ethers.

DETAILED DESCRIPTION OF THE INVENTION

The polyfunctional intermediate, 3-aminophenol, is an important intermediate in the preparation of dyes, agricultural chemicals, pharmaceuticals and polymer intermediates. In particular it is of interest in producing 3',4-oxydianiline which is of extreme importance as an intermediate for aramid and other polymers. It was the object of this invention to produce 3-aminophenol in a practical way and of such purity and condition where it can be used directly, without purification to produce 3,4'-oxydianiline. More Specifically, it was the object of this invention to develop a commercial process for 3-aminophenol from 3-amino-2-cyclohexene-1-one which maximized productivity by improving volumetric efficiency, minimizing the amount of catalyst required, in a manner that the product would need a minimum of purification and could be used directly on the synthesis of other derivatives. It was also the object to develop an improved process for 3-amino-4'-nitrodiphenyl ether and 3,4'-oxydianiline.

This invention involves starting with 3-amino-2-cyclohexene-1-one prepared as described, for example, in Du Pont's application Ser. No. 07/685,359 entitled METHOD FOR MANUFACTURING 3-AMINO-2-CYCLOHEXENE-1-ONE, AND A NOVEL POLYMER INGREDIENT AND ITS PREPARATION, (now U.S. Pat. No. 5,149,874) the teachings of which are incorporated herein by reference. It will be appreciated by those skilled in the art that any commercially prepared 3-amino-2-cyclohexene-1-one or its derivatives may be used as a starting reactant as long as it is sufficiently pure and dehydrogenating it with a palladium catalyst in a solvent in the presence of a base. The addition of base greatly increases the yield of 3-aminophenol and the reaction requires much less solvent and catalyst, thus making the process extremely attractive from a commercial viewpoint. When the solvent is a tertiary amide, the reaction mass may be condensed directly with a halonitrobenzene to produce 3'-amino-4-nitrodiphenyl ether in good yield and quality. This may be readily reduced by standard procedures well known in the art to give 3',4-oxydianiline.

The use of base in the dehydrogenation produces dramatic increases in the yield of 3-aminophenol. For example, when there is no base or when sodium chloride is added as a salt the yield is less than 18%. Addition of a base under the same conditions increases the yield to greater than 80%, depending on the amount and type of base used. This is readily seen in Table I where the base used is potassium acetate. All runs were identical except that the amount of added potassium acetate was changed.

TABLE I

Effect of Potassium Acetate Concentration on the Yield of 3-Aminophenol from 3-Amino-2-cyclohexene-1-one in N-Methylpyrrolidone

| Example | KOAc (Mole/ Hole 3ACO) | % Yield 3-Aminophenol |
|---|---|---|
| 2 | 0(control) | 15 |
| 3 | 0.0005 | 40 |
| 4 | 0.0009 | 74 |
| 5 | 0.0015 | 80 |
| 6 | 0.004 | 78 |
| 7 | 0.013 | 76 |
| 8 | 0.026 | 71 |
| 9 | 0.039 | 61 |
| 10 | 0.117 | 63 |
| 11 | 0.352 | 43 |

From Table I, the optimum amount of potassium acetate ranges from about 0.001 to 0.01 moles/mole of 3-amino-2-cyclohexene-1-one, although broader ranges all produce increased yields.

A variety of bases can be used in this process to produce increased yields. Table II show examples of the range of bases which can be used. All runs were made with 0.004 mole of base per mole of 3-amino-2-cyclohexene-1-one using the same procedure as in Table I.

TABLE II

Effect of Different Bases on the Yield of 3-Aminophenol

| Example | Base | % Yield |
|---|---|---|
| 2 (Control) | none | 15 |
| 11 | Potassium acetate | 78 |
| 12 | Sodium Acetate | 66 |
| 13 | Potassium Hydroxide | 84 |
| 14 | Lithium Hydroxide | 78 |
| 15 | Calcium Hydroxide | 72 |
| 16 | Sodium Hydroxide | 79 |
| 17 | Sodium Methoxide | 77 |
| 18 | Ammonium Hydroxide | 29 |
| 19 | 1,4-diazacyclo-(2,2,2,)octane | 35 |
| 20 | Tri-butyl phosphine (0.0013 mole) | 33 |
| 21 | Sodium Chloride (Control) | 18 |

As can be seen from Tables I and II, any base, inorganic or organic improves the reaction yield. From a practical point of view, the more soluble inorganic bases are preferred from a cost and yield standpoint.

Solvents selected for the reaction are generally aprotic and high boiling and which are good solvents for the reactants and the added bases. These include the tertiary amides N-methyl pyrrolidone (NMP), dimethylacetamide (DMAC), and high boiling oxygenated solvents such as the polyglycols and their ethers. The convenient temperature of the reaction depends on the boiling point of the solvent. The effect of added base in these solvents is shown in Table III.

TABLE III

Effect of Added Base (0.004 mole) in Different Solvents

| Solvent | Temp. °C. | Base % Yield 3-Aminophenol |
|---|---|---|
| NMP | 208 | none 15 |
| NNP | 208 | KOAc 78 |
| DMAC | 165 | none 31 |
| DMAC | 165 | KOAc 59 |
| Triglyme | 195 | none 19 |
| Triglyme | 195 | KOAc 50 |

As the catalyst for the reduction of 3-amino-2-cyclohexene-1-one, palladium or a palladium-platinum mixture on a support such as activated carbon is the preferred choice. The concentration of the palladium on the support can be 0.1 to 20%, preferably 1 to 5% and the platinum concentration can be 0.01 to 5%, preferably 0.05 to 1%. The concentration of the catalyst in the reaction mass is $10^{-5}$ to 5 wt. %. preferably $10^{-3}$ to 1 wt. %. The amount used effects the economics and the smallest amount required is used to achieve reaction rates satisfactory for a commercial process.

The catalyst may also be on other supports than carbon. If basic or alkaline supports such as barium carbonate or strontium carbonate are used, the support can serve as the basic catalyst. In these cases little or no added base is required to produce the increased yields of this invention.

The temperature required for the reaction can range from 130°–350° C., but 160°–250° C. is preferred.

The 3-aminophenol, when prepared according to the above methods in a tertiary amide solvent such as NMP or DMAC, after removal of the catalyst by filtration or centrifugation, may be used directly, without purification, for the synthesis of 3-aminodiphenyl ethers using standard techniques. For example, adding the solution of 3-aminophenol in DMAC to p-chloronitrobenzene, adding potassium carbonate, heating to 170° C. to remove some solvent and volatiles, cooling and removal of salts by filtration, gives 3'-amino-4-nitrodiphenyl ether in solution. After hydrogenation of the solution with additional palladium on carbon catalyst at 100 psig. hydrogen, the solvent and forecut are removed by distillation and the pure product 3,4'-oxydianiline is distilled at 210° C. at 1.5 mm Hg. The overall yield is >60% based on 3-amino-2-cyclohexene-1-one.

All of the prior art procedures start with purified 3-aminophenol in contrast to the present invention where the quality of the crude aminophenol produced from 3-amino-2-cyclohexene-1-one is sufficiently pure to use directly in the condensation with p-nitrochlorobenzene to produce the corresponding ether in good quality. It is obvious from the art cited above that most processes that produce 3-aminophenol contain detrimental amounts of by-products which must be removed before further use. The current process produces 3-aminophenol which can be used directly for further reactions without resorting to complex and expensive purification methods.

The following examples serve to illustrate the invention, but are not intended to limit the scope of the invention.

EXAMPLE 1

The data in Tables I, II, and III (Examples 2-21) was obtained by the following general procedure:

A sample of 3-amino-2-cyclohexene-1-one (1.0 g, 9.0 mmol), potassium acetate or one of the other bases listed in Table II at the molar ratios specified, and 5% palladium on carbon (0.028 g, 0.013 mmol) were added to N-methylpyrrolidinone (2.8 g) or an equal amount of one of the other solvents in a 3-neck 25-cc round bottom flask equipped with a nitrogen inlet, condenser, and thermometer. The solution was initially purged with nitrogen for fifteen minutes and then heated to reflux for 1.5 hours with a continuous nitrogen purge. The solution was then cooled and the yield of 3-aminophenol was determined by gas chromatography using toluene as internal standard.

EXAMPLE 22

The reaction described in Example 1 was repeated except 5% palladium on barium carbonate (0.028 g) was used in place of 5% palladium on carbon and no base was added to the N-methylpyrrolidinone solvent. A 61% yield of 3-aminophenol was obtained.

EXAMPLE 23

The reaction described in Example 1 was repeated except 5% palladium on strontium carbonate (0.028 g) was used in place of 5% palladium on carbon and no base was added to the N-methylpyrrolidinone solvent. A 40% yield of m-aminophenol was obtained.

EXAMPLE 24

The reaction described in Example 1 was repeated except 4% palladium-1% platinum on carbon (0.028 g, 0.013 mmol) was used in place of 5% palladium on carbon with potassium acetate (0.0038, 0.0387 mmol) as base in N-methylpyrrolidinone (2.8 g). A 58% yield of 3-aminophenol was obtained.

EXAMPLE 25

The reaction described in Example 1 was repeated except a 1% palladium-0.05% platinum on silica (0.070 g) catalyst, as detailed in application Ser. No. 07/587,879 (now U.S. Pat. No. 5,128,114), was used in place of palladium on carbon with potassium acetate (0.0038 g, 0.0387 mmol) as base in N-methylpyrrolidinone (2.8 g). A 78% yield of 3-aminophenol was obtained.

EXAMPLE 26

The following example illustrates the conversion of 3-amino-2-cyclohexene-1-one to 3,4'-oxydianiline.

3-Amino-2-cyclohexene-1-one (1.5 mole, 166.7 g), potassium acetate (6 mmol, 0.6 g), and 5% palladium on carbon (4.7 g, 65.5% water) were added to N,N-dimethylacetamide (475 g) solvent in a one liter creased round bottom flask equipped with a nitrogen purge, thermometer, condenser, distillation head, overhead stirrer, and heating mantle. The solution was then heated to reflux for two hours at 173° C. with a continuous nitrogen purge. The palladium catalyst was filtered from the solution. Gas chromatography analysis indicated 130.9 g 3-aminophenol (1.2 mole, 80% yield based on 3-amino-2-cyclohexene-1-one).

The crude solution was then added to 4-chloronitrobenzene (204.8 g, 1.3 mole) and potassium carbonate (124.4 g, 0.9 mole) in a one liter round bottom flask equipped as above and refluxed at 167° C. for 2.5 hour. Water was removed during the first 0.5 hour as the temperature approached reflux. The solution was cooled to 120° C. before filtering through a course filter. The salts were washed with 50 g N,N-dimethylacetamide.

The solution together with 0.4 g 5% palladium on carbon (65.5% in water) were then charged into a one liter autoclave. The autoclave was purged with nitrogen for fifteen minutes followed by a constant 100 psig hydrogen pressure at 125° C. for 3.0 hour. The palladium catalyst was filtered at room temperature. After the solvent was distilled, a forecut was removed at 200° C. and 1.5 mm Hg vacuum before distillation at 210° C. and 1.5 mm Hg vacuum isolated 185.6 g pure 3,4'-oxydianiline (0.9 mole, 60% yield based on 3-amino-2-cyclohexene-1-one.

EXAMPLE 27

The following example illustrates the total process for the preparation of 3-aminophenol starting with m-phenylenediamine, i.e., 1,3-diaminobenzene.

A one liter agitated autoclave was charged with m-phenylenediamine (162.2 g., 1.5 moles), acetic acid (180 g, 3.0 moles), water (225 g) and 5% palladium on carbon, 55% in water (4.8 g) and was purged with nitrogen. Hydrogen was added by pressuring at 140 psig for 3 hours at 60° C. The reaction was cooled to room temperature, vented, and the catalyst was removed by standard methods. The clarified reaction mass was cooled to 0° C. and powdered potassium hydroxide (177 g, 3.1 moles) was added slowly. The agitated mixture was heated to 50° C. and held two hours and then was cooled to room temperature. The precipated product was filtered and was dried under vacuum. The yield was 145.1 g (1.3 moles, 87% theory of 3-amino-2-cyclohexene-1-one. This material was used directly as starting material in Example 26 without purification. Additional potassium acetate may or may not be necessary for the dehydrogenation.

What is claimed is:

1. A method for the preparation of 3,4'-diaminodiphenyl ether comprising the partial reductive hydrogenation of 1,3-diaminobenzene to the acid salt of 3-amino-2-cyclohexene-1-imine, removing the catalyst, followed by hydrolysis at pH>12 to form 3-amino-2-cyclohexene-1-one, followed by dehydrogenating 3-amino-2-cyclohexene-1-one to 3-aminophenol in the presence of a noble metal catalyst in a solvent and introducing a catalytic amount of base into the reaction mass; then heating said reaction mass at a temperature in the range of about 130° C. to about 350° C., followed by condensing 3-aminophenol with a 4-nitrohalobenzene without purification of the intermediate 3-aminophenol, and reduction of the nitro group.

2. The method of claim 1 wherein the solvent is a tertiary amide.

3. The method of claim 2 wherein the transition metal catalyst is selected from the group consisting of palladium on activated carbon, palladium-platinum mixture on activated carbon, palladium-platinum mixture on silica, palladium on barium carbonate and palladium on strontium carbonate.

4. The method of claim 3 wherein the base is selected from the group consisting of potassium acetate, sodium acetate, potassium hydroxide, lithium hydroxide, calcium hydroxide, sodium hydroxide, sodium methoxide, ammonium hydroxide, 1,4-diazacyclo-(2,2,2)-octane, tributyl phosphine.

* * * * *